United States Patent [19]
Tanigawa et al.

[11] Patent Number: 5,353,116
[45] Date of Patent: Oct. 4, 1994

[54] DEFECT INSPECTION SYSTEM FOR PHASE SHIFT MASKS

[75] Inventors: Makoto Tanigawa, Kita; Hiroki Tabuchi; Hiroyuki Moriwaki, both of Nara; Takayuki Taniguchi, Tenri, all of Japan

[73] Assignee: Sharp Kabushiki Kaisha, Osaka, Japan

[21] Appl. No.: 975,681

[22] Filed: Nov. 13, 1992

[30] Foreign Application Priority Data

Nov. 21, 1991 [JP] Japan ................. 3-306170

[51] Int. Cl.$^5$ .............................. G01B 11/24
[52] U.S. Cl. .................................. 356/390
[58] Field of Search .............. 356/390, 394, 237

[56] References Cited
U.S. PATENT DOCUMENTS 5,235,400  8/1993  Terasawa et al. ............ 356/237
5,270,796 12/1993  Tokui et al. .................. 356/398

FOREIGN PATENT DOCUMENTS 62-50811  4/1982  Japan .

OTHER PUBLICATIONS

"Phase Shift Mask Pattern Accuracy Requirements and Inspection Technology", by James N. Wiley et al. no date.

*Primary Examiner*—Richard A. Rosenberger
*Attorney, Agent, or Firm*—Nixon & Vanderhye

[57] ABSTRACT

In the system according to the present invention detects defects by projecting illumination light for exposure having a certain wavelength perpendicularly onto a phase shift mask to be examined; picking up, by means of an image acquisition section, two pattern images which are formed from the irradiated light having passed through two neighboring dies on the phase shift mask and image-formed individually through respective magnifying projection optical systems, and superposing the image patterns of two dies through an alignment to compare therebetween.

12 Claims, 9 Drawing Sheets

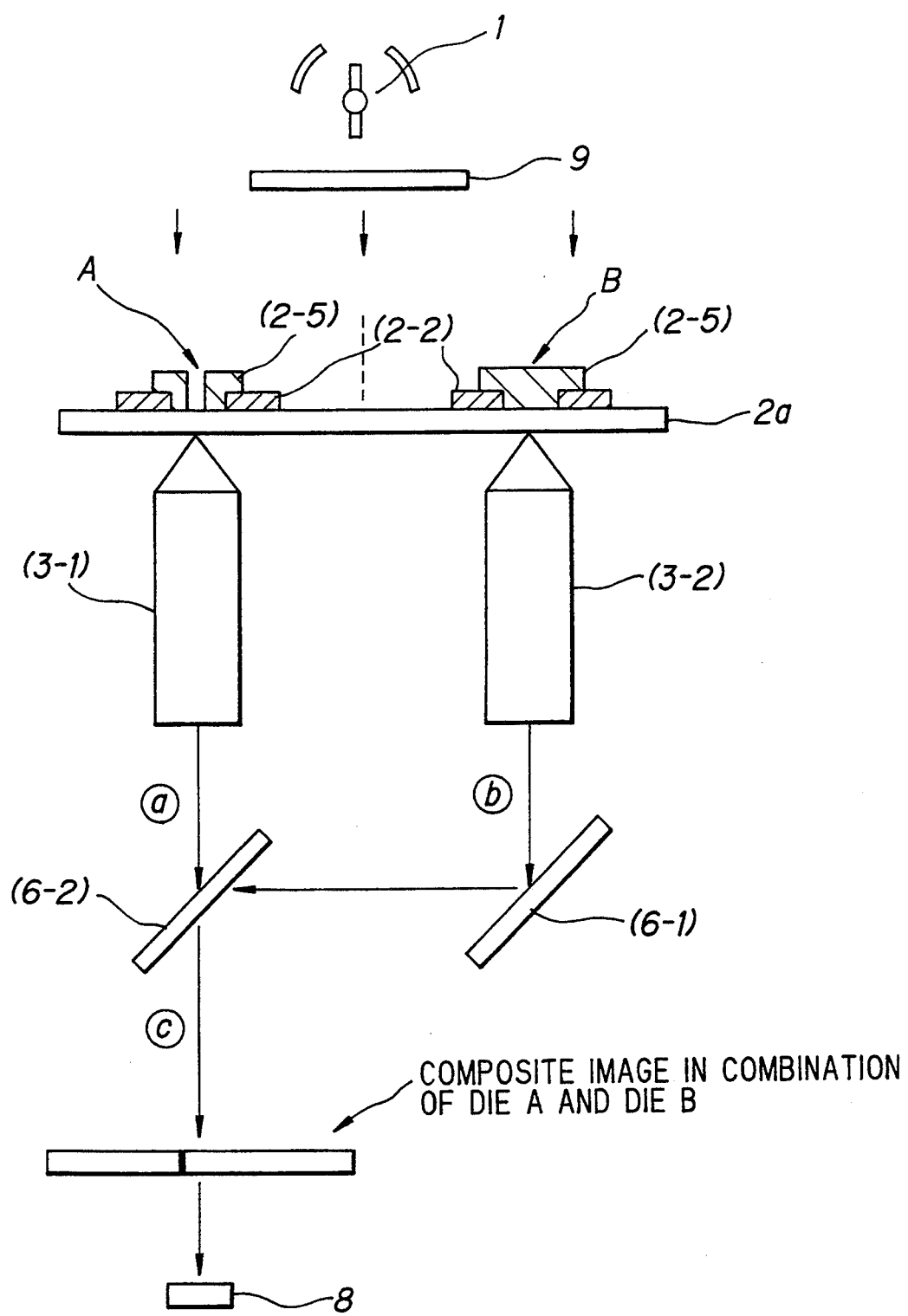

PHASE AMPLITUDE OF
TRANSMISSION LIGHT AT (a)

PHASE AMPLITUDE OF
TRANSMISSION LIGHT AT (b)

PHASE REVERSED BY PHASE FILTER 10

PHASE AMPLITUDE OF
TRANSMISSION LIGHT AT (c)

POSITION OF DEFECT

PHASE AMPLITUDE OF
TRANSMISSION LIGHT AT (d)

DEFECT INSPECTION SYSTEM FOR PHASE SHIFT MASKS

BACKGROUND OF THE INVENTION

1. Field of the Invention

The present invention relates to a defect inspection system for photomasks used in transferring reduction patterns of electronic circuit and/or lines or interconnections onto a crystalline substrate, and more particularly, to a defect inspection system for photomasks, in particular phase shift masks for use in reduction pattern transfer on the order of a submicron.

2. Description of the Related Art

In recent technology very large scale integrated (VLSIA) circuits integrate from hundreds of thousands to several million transistors and interconnections of submicron order on the surface of a single chip silicon crystalline substrate. These fine transistors and lines are patterned by a photolithography process in which a pattern of submicron order is formed, reduced, and then transferred on (a smaller scale [one-fourth to one-tenth]) onto a silicon substrate with a photoresist layer applied thereon.

More specifically, the photolithographic process comprises the steps of arranging transparent portions and opaque portions formed with Cr film and the like on a photoresist layer applied on a crystalline substrate (for example, a silicon crystalline substrate), and irradiating illumination light onto a photoresist mask of a certain pattern so as to transfer a mask pattern (that is, a pattern reduced on a scale of ¼ to 1/10 from an original pattern by means of a reducing projection exposure device). In the current mass-production, 1 megabit and 4 megabit DRAM's (abbreviation of Dynamic Random Access Memory), are patterned with lines having a minimum line width of 1.2 $\mu$m and 0.8 $\mu$m, respectively. In the photolithography to form patterns having such linewidths, the illumination light irradiated onto photomasks employed, in most cases, is a g-line (a bright emission line having a wavelength of 436 nm) which is radiated from an extra-high pressure mercury lamp. However, recently an i-line (bright emission line having a wavelength of 365 nm) emitted from the same mercury lamp has also been used.

The anticipated minimum line widths for use in 16 megabit DRAM's and 64 megabit DRAM's (which are expected to be fabricated in the future) are estimated to be 0.6 to 0.5 $\mu$m and 0.4 to 0.3 $\mu$m, respectively. In order to achieve the mass production of these semiconductor devices, it is first necessary to form photomasks having such minimum line widths, and this requires increased photo-lithography in its resolution. To deal with this requirement, or in order to improve the resolution by using light of shorter wavelengths, not only has there been use of i-line (in place of g-line) investigated and discussed but also employment of a krypton-fluorine exciter laser having a shorter wavelength, e.g. of 248 nm.

The photolithography using the above-discussed conventional photomasks, however, has a following drawback. That is, a pattern image formed by a transparent portion of a photomask on the photoresist layer of a crystalline substrate as a mask pattern is difficult to separate from that by a neighbor transparent portion, due to the interference between the diffracted light from the the edge of the first transparent portion and that from the edge of the neighbor transparent portion.

A resolution of a step and repeat photolithographic system with demagnification is determined in theory by a numerical aperture NA and the wavelength $\lambda$ of the illumination light. However, for the reason just mentioned above, the resolution obtained in practice is by far inferior to the theoretical value.

A photomask for overcoming the difficulty stated above is proposed in Japanese Patent Application Laid-Open No. Sho-57-62052 (1982), laid open on Apr. 14, 1982, invented by Masato Shibuya, the title of which is "A Photomask to be Projected by a Transmissive Illumination."

In that invention, i.e. "A Photomask to be Projected by a transmissive Illumination", a photoresist mask is proposed which is constructed such that a predetermined pattern with transparent portions and opaque portions, and at least one of transparent portions between which an opaque portion is located is provided with a phase shift member (for example a 180° phase shifter) so as to cause a phase difference between the nearest neighboring transparent portions.

Another report is "Improving Resolution in Photolithography with a Phase-Shifting Mask" by M.D.Levenson et al. appears in "IEEE Transactions on Electron Devices" Vol. ED-29 No. 12, p.p 1828–1846, 1982"published by Institute of Electrical and Electronics Engineers in U.S.A. This article reported in effect that use of a photomask having a similar phase member (i.e. 180° phase-shifting member) with that disclosed by the aforementioned Japanese Patent Application Laid-Open No.sho-57-62052 (1982) aforementioned, increases resolution and depth of focus in photolithography.

Further, a study on submicron resist exposures and simulations of transfer image was made by M.D. Levenson et al. and reported in "The Phase Shifting Mask II: Imaging Simulations and Submicron Resist Exposures" in IEEE Transactions on Electron Devices, Vol. ED-31, No. 6(1984) pp. 753–763.

In accordance with the photolithographic technique using a phase shift mask as stated above, it is possible to obtain a high resolution transfer image having a minimum linewidth in the order of submicron. Even if, however, there were a photomask capable of providing a transfer image with a high resolution, if the mask in itself has defects (such as, for example, a protrusion, or cracked portion, at an edge of or inside, a transparent portion of a phase shift member) the mask could not be used for the photolithography. Accordingly, it is necessary to control the photoresist mask before operation such that the presence and absence of defects is inspected on the phase shift mask to be used, so that the mask can be discarded if it there is a defect.

As regards detection of defects in a phase-shift mask, there is a report of James N. Wiley et al., entitled "Phase-Shift Mask Pattern Accuracy Requirements and Inspection Technology", included in a lecture preparation text "Integrated Circuit Metrology, Inspection, and Process Control V", William H. Arnold, Editor, Proc SPIE 1464, pp. 346–355 (1991)" published by The International Society for Optical Engineering (SPIE for abbreviated name). According to this article, the evaluation was carried out by KLA 219 HR-PS prototype die-to-die photomask inspection system. The inspection system mentioned immediately above is constructed as shown in FIG. 1. Specifically, illumination light emitted from a mercury lamp 1 is irradiated onto a phase shift mask 2 formed with a certain mask pattern having, for example, two neighboring dies A, B. The transmitted light carrying the image patterns of these two dies A, B is individually introduced to respective optical systems (3-1) and (3-2) for projection. The thus transmitted light through the optical systems, passing through an image acquisition device 4 (including a charge coupled device and the like), is then filtered by noise removal filter 5 to be provided to an alignment device 6. Two image patterns of dies A, B are overlapped or superposed on one another in the alignment device 6 so as to detect (by means of defect detection section 7) the presence of defects in the transparent area on the phase shift mask 2.

The phase shift mask 2a examined by the KLA219HR-PS prototype die-to-die photomask inspection system shown in FIG. 1, includes (as shown in FIGS. 2A and 2B, for example), on a transparent quartz wafer 2 a resist layer (2-3) applied thereon, opaque Cr films (2-2), (2-2) adhered apart from each other by a certain distance, an isolated Cr film (2-4), a self-aligned phase mask which is formed with a phase shift layer (2-5) for sharping the contour of the Cr film (2-4), and has a larger area than that of the Cr film (2-4).

The inspection system shown in FIG. 1 comprises a light source for exposure illumination (e.g. a mercury lamp) 1; projection optical systems (3-1), (3-2) for projecting and image-forming the illumination "light transmitted through respective dies A, B on the phase shift mask onto an image acquisition section 4; a noise removal filter 5 (for removing noise from the data signals of the images representing the dies A, B, and projected on the image acquisition section 4); an alignment device 6 for receiving the image data signals of the dies A, B (noise-freed by means of the noise removal filter 5, so as to superpose the image patterns of dies A and B); and a defect detection section 7 for receiving the image pattern data overlapped in the alignment 6 to be stored in advance and comparing the pattern data of a phase shift mask under test, so as to detect defects on the phase shift mask under test.

In this inspection system, the same detection operations as in the examination on two dies A and B of the phase-shift mask under test will be repeated successively with respect to other pairs of dies to complete defect inspection for every die on the entire phase shift mask.

In the inspection system described above, since the illumination light (a mercury lamp in FIG. 1) generally consists of polychromatic light, scattering at an edge of a transparent portion in a phase shift mask is not constant. As a result it is impossible to obtain an accurate detection sensitivity to defects. The inspection system of this type has a defect inspection capability or resolution of about 400 nm, which is inferior to the defect inspection capability for metal masks used in the same semiconductor manufacturing process. Here, the metal mask indicates an exposure mask having a predetermined pattern of opaque metal films arranged on the transparent quartz wafer by separating one another with providing light-transmissive clearances having a certain width.

From a manufacturing view point, however, a defect on a phase-shift mask is more likely to be transferred than that on a metal mask. For this reason, the criteria for the defect inspection for phase-shift masks is more stringent than for that of metal masks.

Moreover, in the inspection system shown in FIG. 1 above, a defect is detected by means of scattered light, therefore, defects along edges of transparent portions alone can be detected, but those inside, or enclosed by, a transparent portion are beyond detection., Since defects of phase shift masks may possibly appear not only at the edges of transparent portions but also thereinside, development of a phase shift mask defect inspection system capable of detecting defects in the entire phase-shift mask would be highly desirable.

In addition, in the inspection system of FIG. 1 described above, two dies under test are examined alternately for comparison, so that it takes a long time to examine the patterns. Accordingly, a phase shift mask defect inspection system which can examine both dies simultaneously has long been sought.

BRIEF DESCRIPTION OF THE DRAWINGS

FIG. 6 is a block diagram showing schematic configuration of a defect inspection system for phase shift masks according to a second embodiment of the invention;

SUMMARY OF THE INVENTION

Figure 1:
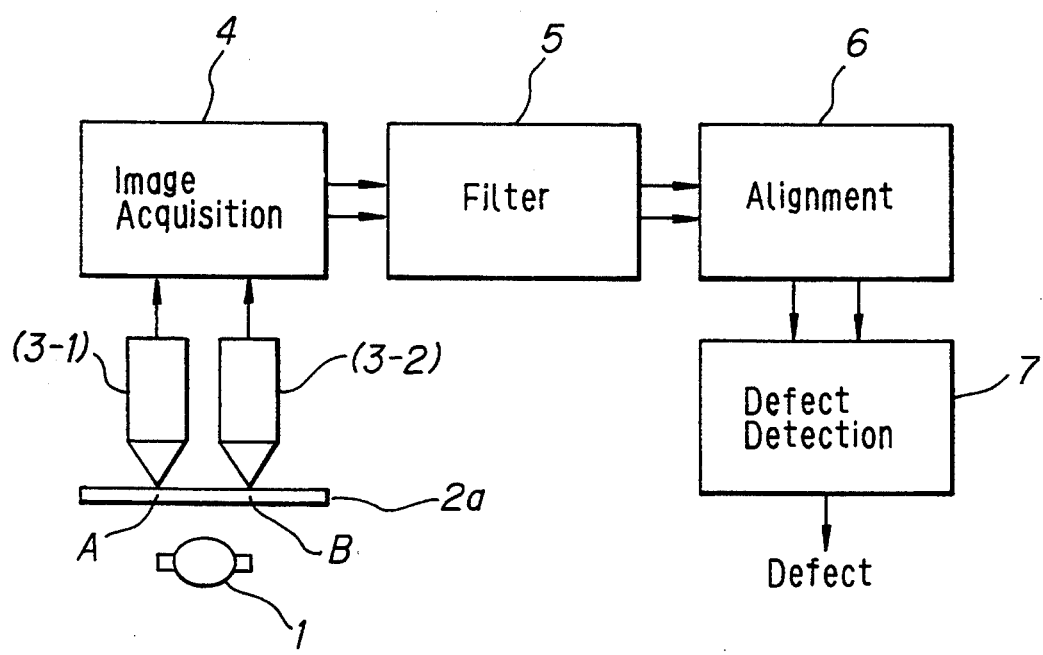
FIG. 1 is a block diagram schematically showing a system construction of a prior art defect inspection system for phase shift mask.
Figure 2A:
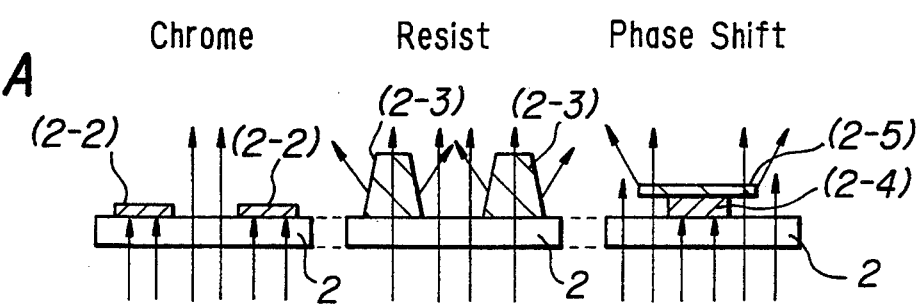
FIG. 2A is a side view showing a phase shift mask to be examined in the defect inspection system for phase shift mask shown in FIG. 1.
Figure 2B:
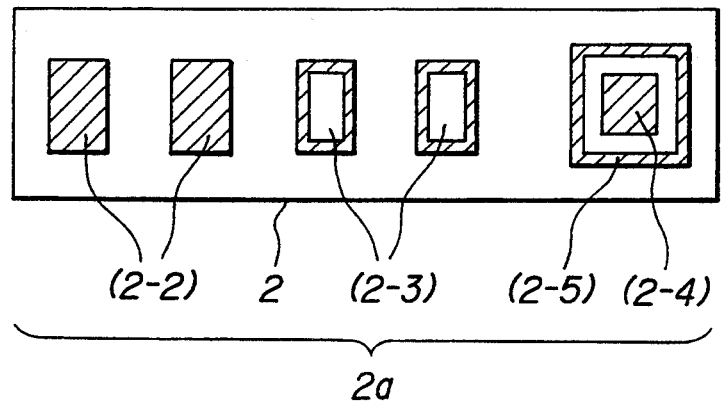
FIG. 2B, is a plan view showing the phase shift mask shown in FIG. 2A.
Figure 3:
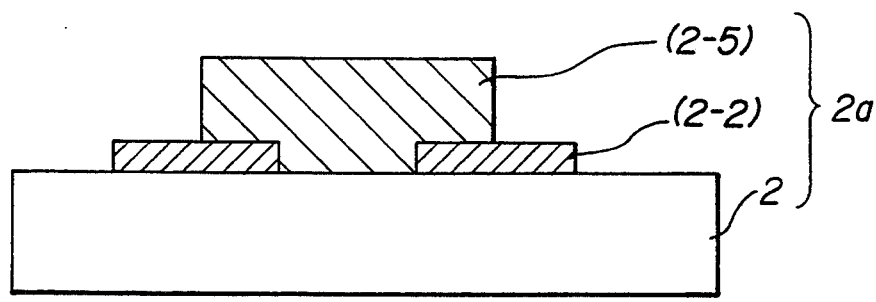
FIG. 3 is a side view showing a state in which a phase shift member is arranged in a transparent portion of the phase shift mask shown in FIGS. 2A and 2B.

The present invention has been achieved under consideration of the above-detailed circumstances of the conventional defect inspection system for phase shift masks. It is an object of the present invention to provide a system capable of precisely detecting (in a short time)

defects located inside a transparent portion as well as defects along the edge of the transparent portion of a phase shift mask.

According to the defect inspection system for phase shift masks of the present invention, the phase shift mask to be examined is projected with monochromatic illumination light having a single wavelength, so that scattering at the edges of a transparent portion can be reduced markedly. With this effect, it is possible to increase detection sensitivity to defects.

In accordance with the defect inspection system for phase shift masks of the present invention, monochromatic light having a single wavelength is irradiated separately onto two neighboring dies on the phase shift mask, and the image patterns of these dies carried by the respective transmitted light are superposed to be compared each other. Accordingly, if either die does not have any defect, the superposed image pattern of the two dies makes a completely white image, and if there is an defect, the portion corresponding to the defect appears as a black spot or stain in a white image. This provide easiness in the detection of defects.

DESCRIPTION OF THE PREFERRED EMBODIMENTS

Preferred embodiments of the present invention will now be described. In the description, the same reference numerals will be allotted to the corresponding members having the same functions to those used in the conventional defect inspection system for phase shift masks shown in FIGS. 1, 2, 3 and 4.

Embodiment 1

Figure 4:
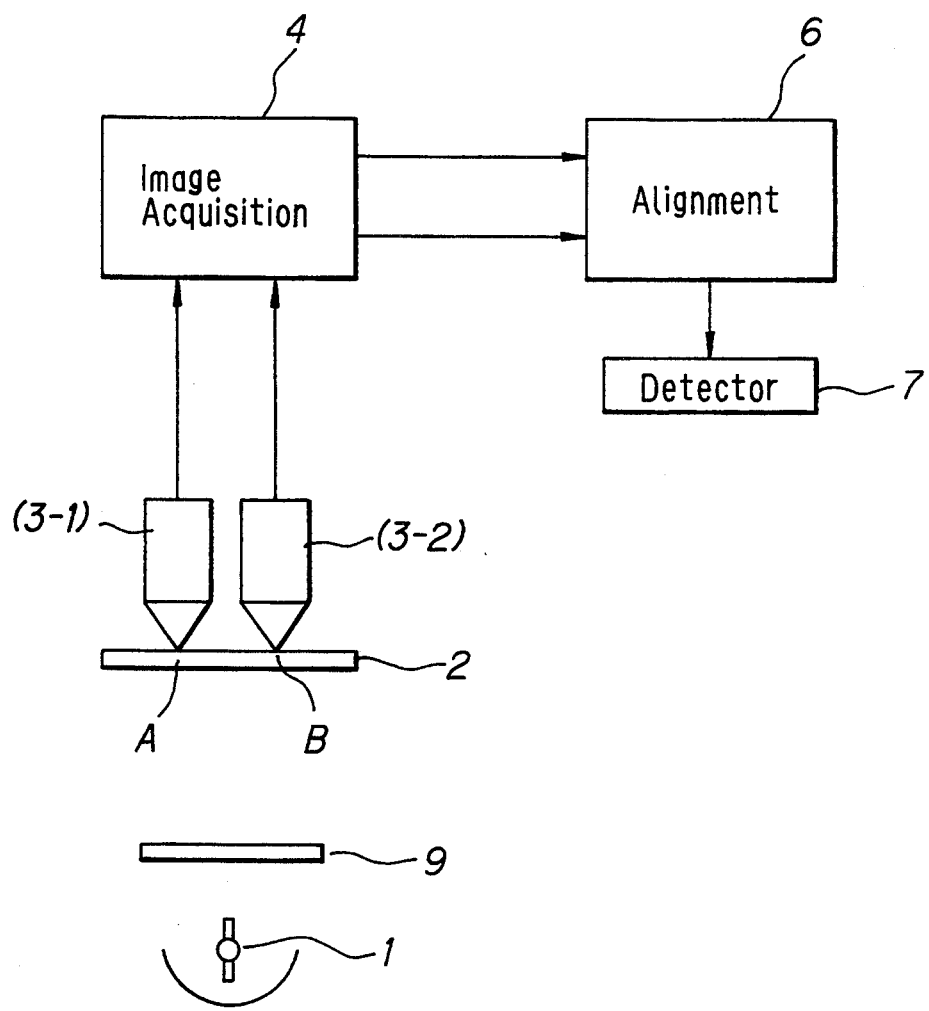
FIG. 4 is a block diagram showing a basic configuration of a defect inspection system for phase shift masks according to the present invention.
Figures 5A, 5B:
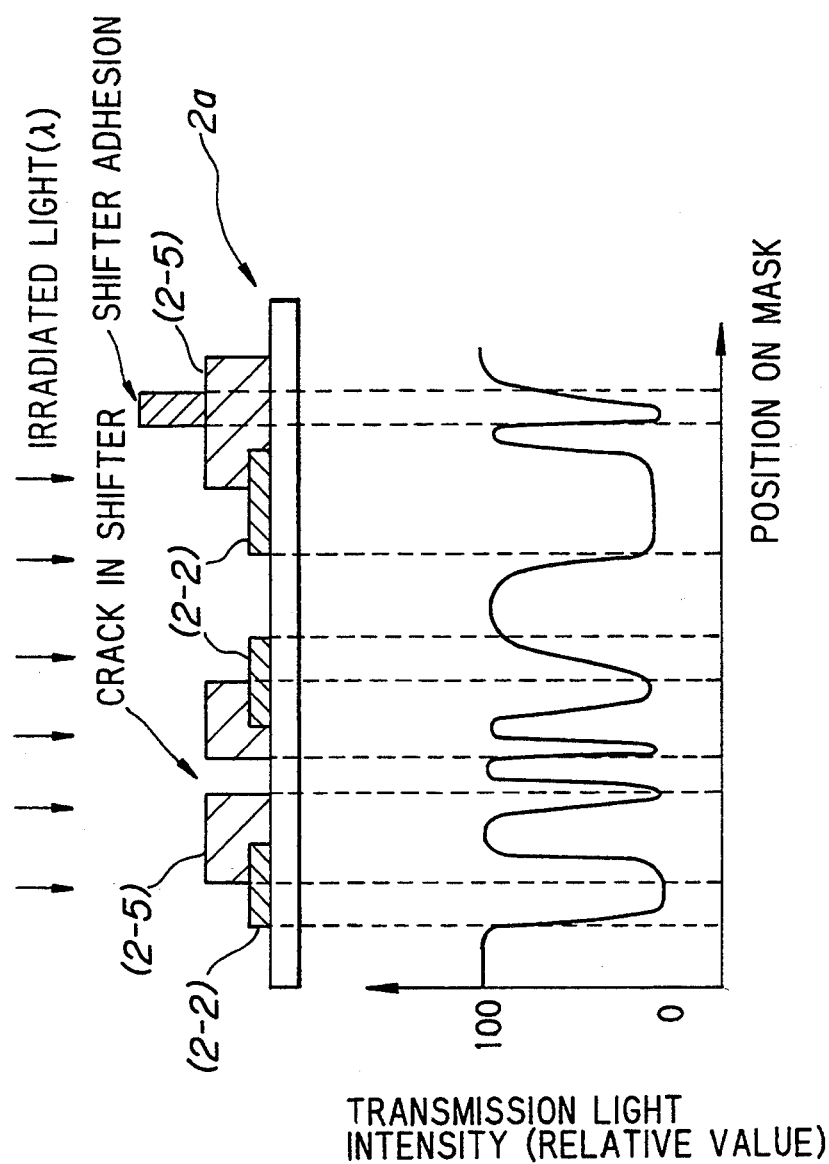
FIG. 5A is a longitudinal sectional view showing a structure of a phase shift mask to be examined in a first embodiment of the invention.
FIG. 5B is a diagram showing a transmitted light intensity distribution of the irradiated light projected on the phase shift mask shown in FIG. 1.

FIGS. 4, is a block diagram of a schematic configuration of a defect inspection system for phase shift masks according to a first embodiment of the invention. FIG. 5A and 5B are (respectively) a sectional view showing a phase shift mask to be examined and a diagram showing the intensity distribution of the light transmitted through the phase shift mask under test.

A phase shift mask 2a to be examined in this embodiment comprises a quartz glass and an opaque film of chromium and a transparent phase shift film (transparent $SiO_2$: index of refraction 1.42). The size of the mask is 5 inches square and 0.09 inch thick, and the transparent $SiO_2$ film is 434 nm in thickness.

In the defect inspection system for phase shift masks of the embodiment, illumination light emitted from a high pressure mercury lamp (1 to 3 arm. Hg) 1 is filtered by a monochrome filter 9 to yield the i-line alone as illumination light for exposure. The thus extracted monochromatic light is projected at right angles onto the surface of the phase shift mask 2a.

The illumination light rays (transmitted light) having separately passed through neighboring dies A and B on the phase shift mask 2a, are introduced to respective magnifying projection optical (lens) systems (3-1) and (3-2) disposed after the phase shift mask 2a. The light rays passed through the optical system are image-formed and projected in an image acquisition section 4.

The image patterns of the dies A and B projected respectively by the magnifying projection optical systems (3-1) and (3-2), although they are not shown in FIG. 4, are superposed on one another by mirrors belonging to an alignment (for example, a reflection mirror (6-1) and a composite half mirror (6-2) shown in FIG. 6), to thereby be introduced into a detection section 8. In the detection section 8, image patterns of the two dies A and B are compared with each other to detect presence of defects. For example, a crack and a shifter adhesion of phase shift members (2-5) are detected on the phase shift mask 2a examined in FIG. 5A.

FIG. 5B shows the intensity distribution of the light transmitted through the phase shift mask 2a. In the figure, there are found apparent dark and bright variations in the intensity of the transmitted light due to the crack and adhered substance on the phase shift member (2-5). The change in the transmitted light intensity occurs more distinctly than that caused by an opaque metal mask defect (pattern defect) having the same size, so that the detection sensitivity can be markedly improved compared with the prior art defect inspection system.

In this embodiment, the projection optical systems (3-1) and (3-2) are constructed by a magnifying type, i.e. magnifying projection optical system, so that a defect is projected as magnified. Therefore, it is possible to detect defective portions in detail with high precision. The magnification aspect projection optical system is not essential, but desirable since the system without is inferior in accuracy.

Embodiment 2

FIG. 6 is a block diagram showing schematic configuration of a defect inspection system for phase shift masks according to a second embodiment of the invention.

Figures 7A, 7B, 7C:
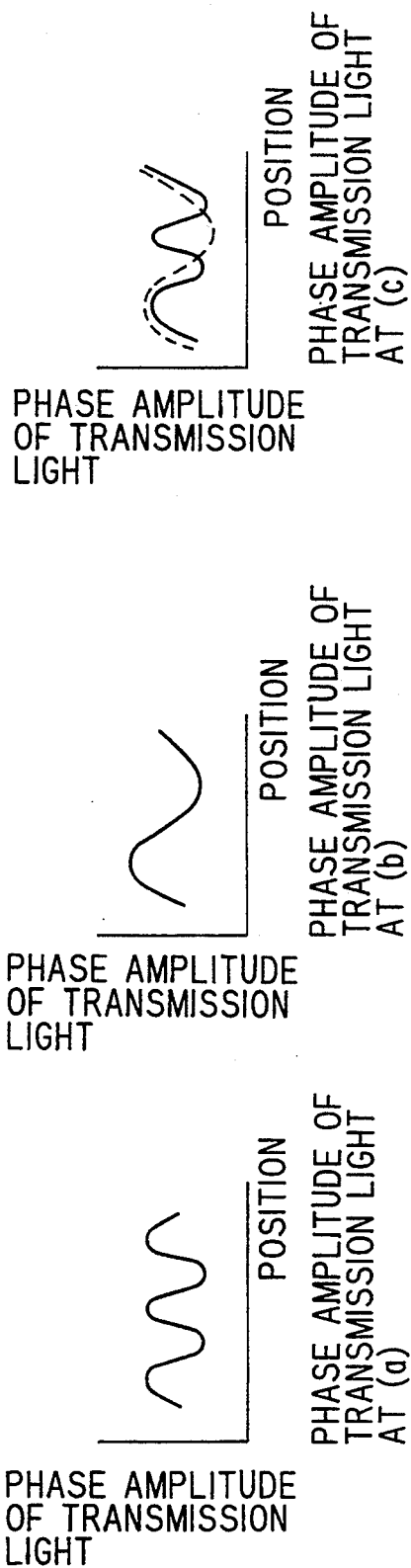
FIGS. 7A, 7B and 7C are charts of characteristic curves showing phase amplitude of transmitted light on respective light paths (a), (b) and (c) of the irradiated light for exposure in the defect inspection system for phase shift mask shown in FIG. 6.

FIGS. 7A, 7B and 7C are charts of characteristic curves showing relations of phase amplitude of the transmitted light on respective light paths (a), (b), and (c) in FIG. 6. Here the light path is a route from a phase shift mask 2a to a composite half mirror (6-2) as a part of the alignment, the light path (b) extends from the phase shift mask 2a through a reflection mirror (6-1) to the composite half mirror (6-2), the light path (c) extends from the composite half mirror (6-2) to a detection section 8. On the light path (c), there can be obtained an image composed by the half mirror (6-2) of pattern images of die A and die B, each image formed passing through respective magnifying projection optical systems.

Figure 8:
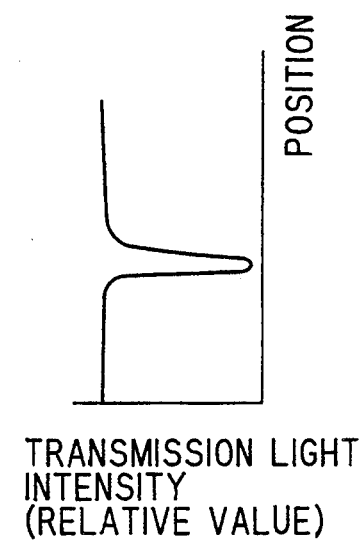
FIG. 8 is a chart of a characteristic curve showing the phase amplitude superposed between image patterns of two dies by an alignment of the defect inspection system for phase shift masks shown in FIG. 6.

FIG. 8 is a chart of a characteristic curve showing the phase amplitude variation of an image pattern superposed by an alignment of the image patterns of the die A and die B.

In the defect inspection system for phase shift mask of this embodiment, as shown in FIG. 6, magnifying projection optical systems (3-1) and (3-2) are disposed downstream of the die A and die B on the phase shift mask under test 2a, respectively. Downstream of the optical systems (3-1) and (3-2) are disposed the reflection mirror (6-1) and composition half mirror (6-2) respectively, for alignment. In addition, downstream of the composite half mirror (6-2) is disposed the detection section 8 for detecting the image pattern formed by superposing image patterns of die A and die B through the composition half mirror (6-2).

In accordance with the system, as shown in FIG. 8, the crack portion on the die A of the phase shift mask 2a is null in its light intensity so as to become black, whereas the light coming from the portions other than the defect or cracked portion is amplified to high intensity, so that it looks white in a composed image. The composed image is sensed by the detection section 8 (a photomal CCD) to be detected as a black spot in the white bright field.

Embodiment 3

Figure 9:
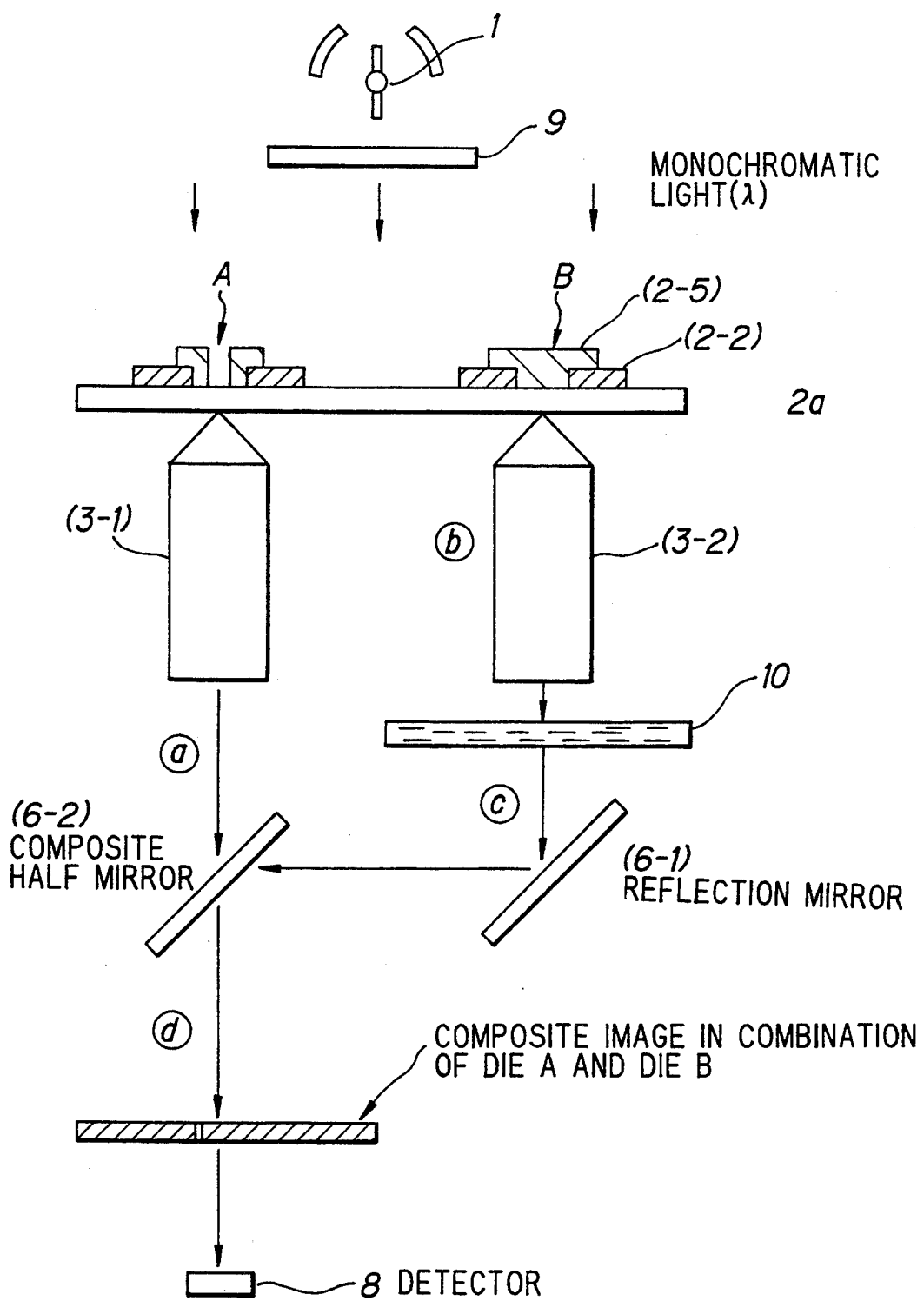
FIG. 9 is a block diagram showing schematic configuration of a defect inspection system for phase shift masks according to a third embodiment of the invention.

FIG. 9 is a block diagram showing schematic configuration of a defect inspection system for phase shift masks according to a third embodiment of the invention. This embodiment has the same construction as the defect inspection system for phase shift masks shown in FIG. 6 except that a phase filter 10 is disposed after the projection optical system (3-2) on the light path of the illumination light transmitted through the die B.

This phase filter 10 generally employs a 180° phase-shifter, but a phase-shifter causing other than a 180° phase-shift may be used. The effect is maximized when the system is arranged such that the phase of the light which is incident onto the die B to pass through a phase shift layer (2-5) and the phase shifter 10 is delayed 180° from the light incident onto the die A.

Figure 10A:
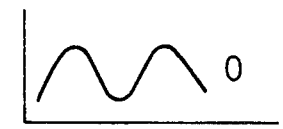
FIGS. 10A, 10B, 10C and 10D are charts of characteristic curves showing phase amplitude of transmitted light on light paths (a), (b), (c) and (d) of the irradiated light for exposure in the defect inspection system for phase shift masks shown in FIG. 9.
Figure 10B:
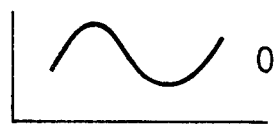
Figure 10C:
Figure 10D:
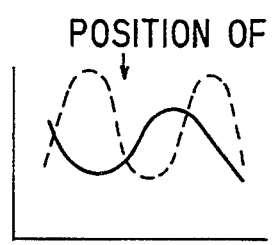
Figure 11:
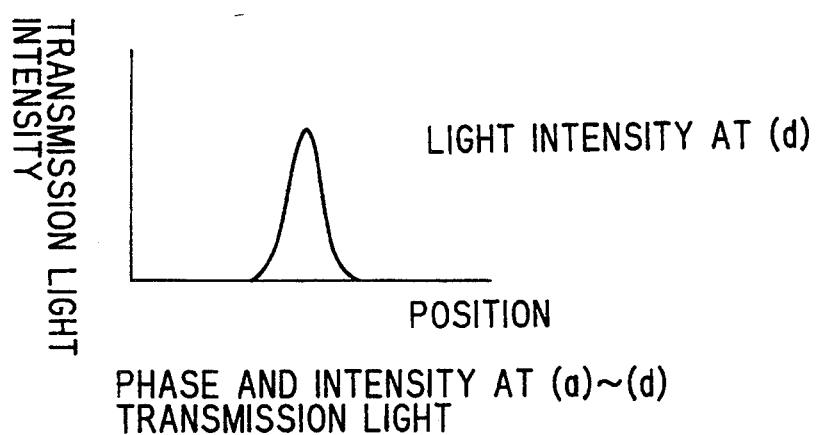
FIG. 11 is a diagram showing a transmitted light intensity distribution on light path (d) of the irradiated light for exposure in the defect inspection system for phase shift masks shown in FIG. 9.

FIGS. 10A through 10D are charts of characteristic curves showing respective phase amplitude of transmitted light on various light paths in the detect inspection system for phase shift masks. More specifically, FIG. 10A shows a phase amplitude of the transmitted light on a light path between the die A of a phase shift mask to be examined in the system and the composite half mirror (6-2) for alignment. FIG. 10B shows a phase amplitude of the transmitted light on a light path between the die B and the projection optical system (3-2). FIG. 10C shows a phase amplitude on a light path between the projection optical system (3-2) and the composite half mirror (6-2). FIG. 10D shows a composed amplitude intensity distribution on the composite half mirror (6-1). FIG. 11 is a chart of a characteristic curve showing a relation between phase amplitude and light intensity at the alignment device 6 (composite half mirror (6-2).

The phase shift mask 2a has a crack inside the phase shift member (2-5) of the die A, so that the composite light intensity in other than the position corresponding to the defect portion become, as shown in FIG. 11, null to make the image black, but the light transmitted through the defect is amplified to a high intensity so that it looks white in a composed image. When the composed image is subjected to the detection section 8 (a photomal CCD), the position corresponding to the defect is detected as a white spot in the dark field.

Although the above descriptions of the embodiments 1 to 3, have been made assuming that the exposure of the phase shift mask under test is carried out with i-line (365 nm) radiated from the high pressure mercury lamp, this should not limit the invention, and it is also under consideration to use G-line (436 nm), and ultra-violet rays such as a 253.7 nm bright line emitted from a low pressure mercury having a pressure of 0.01 to 0.1 mmHg, a 248 nm radiation of a Kr-F excimer laser, a 193 nm radiation of a Ar-F excimer laser and the like.

What is claimed is:

1. A defect inspection system for phase shift masks comprising:
   a light source for irradiating light perpendicularly onto a surface of a phase shift mask to be examined, the mask having a pair of dies that are identical except for possible flaws;
   a monochromatic light selection means disposed between said light source and the phase shift mask for filtering and separating light having a certain wave length from the light emitted by said light source;
   a pair of projection optical systems each of which forms an image pattern of the irradiated light having passed through a corresponding one of the dies and which projects the formed image pattern;
   means for forming a superposed image of the image patterns formed by the pair of projection optical systems; and
   a detection section for detecting defects on the phase shift mask to be examined by processing the superposed image.

2. A defect inspection system for phase shift masks according to claim 1, wherein each of said pair of projection optical systems is a magnifying projection optical system.

3. A defect inspection system for phase shift masks according to claim 1, wherein the means for forming a superposed image of the image patterns is a composite half mirror.

4. A defect inspection system for phase shift masks comprising:
   a light source for irradiating light perpendicularly onto the surface of a phase shift mask to be examined, the mask having a pair of dies that are identical except for possible flaws;
   a monochromatic light selection means disposed between said light source and the phase shift mask for filtering and separating light having a certain wave length from the light emitted by said light source;
   a 180° phase shift means disposed on an optical path of the irradiated light after a first of the pair of dies;
   a pair of projection optical systems, a first of which forms a first image of the irradiated light for exposure transmitted through said 1800 phase shift means and projects the formed first image, and a second of which forms a second image of the irradiated light having passed through a second die of the pair of dies and projects the formed second image;
   means for forming a superposed image of the first image and the second image; and
   a detection section for detecting defects on the phase shift mask by processing the superposed image.

5. A defect inspection system for phase shift masks according to claim 4, wherein each of said projection optical systems is a magnifying projection optical system.

6. A defect inspection system for phase shift masks according to claim 4, wherein the means for forming a superposed image of the image patterns is a composite half mirror.

7. A defect inspection system for phase shift masks comprising:
   a source of monochromatic light source for irradiating light perpendicularly onto a surface of a phase shift mask to be examined, the mask having a pair of dies that are identical except for possible flaws;
   a pair of projection optical systems each of which forms an image pattern of the irradiated light having passed through a corresponding one of the dies and which projects the formed image pattern;
   means for forming a superposed image of the image patterns formed by the pair of projection optical systems; and
   a detection section for detecting defects on the phase shift mask to be examined by processing the superposed image.

8. A defect inspection system for phase shift masks according to claim 7, wherein each of said pair of projection optical systems is a magnifying projection optical system.

9. A defect inspection system for phase shift masks according to claim 7, wherein the means for forming a superposed image of the image patterns is a composite half mirror.

10. A defect inspection system for phase shift masks comprising:
- a monochromatic light source for irradiating light perpendicularly onto the surface of a phase shift mask to be examined, the mask having a pair of dies that are identical except for possible flaws;
- a 180° phase shift means disposed on an optical path of the irradiated light after a first of the pair of dies;
- a pair of projection optical systems, a first of which forms a first image of the irradiated light for exposure transmitted through said 180° phase shift means and projects the formed first image, and a second of which forms a second image of the irradiated light having passed through a second die of the pair of dies and projects the formed second image;
- means for forming a superposed image of the first image and the second image; and
- a detection section for detecting defects on the phase shift mask by processing the superposed image.

11. A defect inspection system for phase shift masks according to claim 10, wherein each of said projection optical systems is a magnifying projection optical system.

12. A defect inspection system for phase shift masks according to claim 10, wherein the means for forming a superposed image of the image patterns is a composite half mirror.

* * * * *